United States Patent [19]

Bank

[11] Patent Number: 5,103,033
[45] Date of Patent: Apr. 7, 1992

[54] PROCESS FOR PREPARATION OF β-CYANOALKYLSILANES

[75] Inventor: Howard M. Bank, Freeland, Mich.

[73] Assignee: Dow Corning Corporation, Midland, Mich.

[21] Appl. No.: 719,454

[22] Filed: Jun. 24, 1991

[51] Int. Cl.$^5$ ............................................. C07F 7/10
[52] U.S. Cl. .................................... 556/415; 556/479
[58] Field of Search .................................... 556/415

[56] References Cited

U.S. PATENT DOCUMENTS

| | | | |
|---|---|---|---|
| 2,860,153 | 11/1958 | Saam | 556/415 |
| 2,906,764 | 9/1959 | Jex et al. | 556/415 |
| 2,906,765 | 9/1959 | Jex et al. | 556/415 |
| 2,971,970 | 2/1961 | Bluestein | 556/425 |
| 2,971,972 | 2/1961 | Bluestein | 556/45 |

OTHER PUBLICATIONS

Rajkumar et al., Organometallics 8, 550-552, 1989.
Svoboda et al., Collection Czechoslov. Chem. Commun. 38, 3834-3836, 1973.

Primary Examiner—Paul F. Shaver
Attorney, Agent, or Firm—William F. Boley

[57] ABSTRACT

The present invention is a process for the preparation of hydrolyzable β-cyanoalkylsilanes. More particularly, this invention relates to the catalytic addition of silicon hydrides to α,β-unsaturated olefinic nitriles to form β-cyanoalkylsilanes. The instant process employs a catalyst comprising a diamine and copper or a copper compound. The copper or copper compond may be retained on a solid support. The proces rate and yield of β-cyanoalkylsilanes is increased by running the process in essentially an oxygen free environment.

26 Claims, No Drawings

PROCESS FOR PREPARATION OF β-CYANOALKYLSILANES

BACKGROUND OF INVENTION

The present invention is a process for the preparation of hydrolyzable β-cyanoalkylsilanes. More particularly, this invention relates to the catalytic addition of silicon hydrides to α,β-unsaturated olefinic nitriles to form β-cyanoalkylsilanes. The instant process employs a catalyst comprising a diamine and copper or a copper compound. The copper or copper compound may be retained on a solid support. The process rate and yield of β-cyanoalkylsilanes is increased by running the process in essentially an oxygen free environment.

Hydrolyzable β-cyanoalkylsilanes are useful for the production of polyorganosiloxanes containing the β-cyanoalkyl substituent. The silicon-bonded β-cyanoalkyl radical is extremely resistant to hydrolysis and cleavage under hot, humid conditions. Therefore, the β-cyanoalkylsilanes find particular use in the preparation of polyorganosiloxanes which must be subjected to hot humid conditions. The presence of the silicon-bonded β-cyanoalkyl radical substituted on polyorganosiloxanes also tends to stabilize the polyorganosiloxanes against swelling induced by liquid hydrocarbons.

Bluestein, U.S. Pat. No. 2,971,970, issued Feb. 14, 1961, describes a method for forming cyanoalkylsilanes. The method comprises reacting a hydrolyzable silicon hydride with an α,β-unsaturated olefinic nitrile in the presence of a diamine and a cuprous compound selected from the class consisting of cuprous oxide and cuprous halides.

Rajkumar et al., Organometallics 8, 550-552, 1989, describes a two-component catalyst, consisting of cuprous oxide and tetramethylethylenediamine, that promotes β-hydrosilylation of acrylonitrile.

Svoboda et al., Collection Czechoslov. Chem. Commun. 38, 3834-3836, 1973, describes binary systems of a copper compound (Cu(I) oxide, Cu(I) chloride, or Cu(II) acetylacetonate) and an isocyanide (tert-butyl or cyclohexyl isocyanide) as effective catalysts for hydrosilylation of acrylonitrile by trichlorosilane and methyldichlorosilane.

The present invention improves on the prior art for β-hydrosilylation of unsaturated olefinic nitriles by silicon hydrides, in the presence of a catalytic mixture of a diamine and copper or copper compound, by running the process in essentially the absence of oxygen. Removal of oxygen from the system can improve both the rate of product formation and the total yield of product from the process.

SUMMARY OF INVENTION

The present invention is a process for the preparation of hydrolyzable β-cyanoalkylsilanes. More particularly, this invention relates to the catalytic addition of hydrolyzable silicon hydrides to α,β-unsaturated olefinic nitriles to form β-cyanoalkylsilanes. The process employs a catalyst comprising a diamine and copper or copper containing compound. The copper or copper compound may be retained on a solid support. The process rate and yield of β-cyanoalkylsilanes is increased by running the process in essentially an oxygen free environment.

DESCRIPTION OF INVENTION

The present invention is a process for preparation of β-cyanoalkylsilanes of formula:

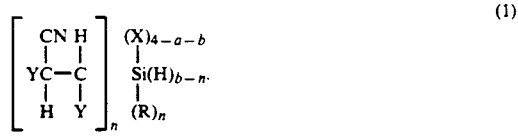

The process comprises contacting, in an essentially oxygen free environment, a silicon hydride of formula

with an unsaturated olefinic nitrile of formula

in the presence of a catalyst comprising a mixture of a diamine of formula

and a copper source selected from a group consisting of copper metal and copper compounds: where each R is independently selected from a group consisting of monovalent hydrocarbon radicals, substituted monovalent hydrocarbon radicals alkoxy radicals, and aryloxy radicals; $R^1$ is a lower alkyl radical; $R^2$ is selected from a group consisting of hydrogen, lower alkyl radicals, aminoalkyl radicals, alkylaminoalkyl radicals, dialkylaminoalkyl radicals, and mixtures thereof; $R^3$ is an unsubstituted bivalent radical selected from a group consisting of alkylenes and alkenylenes of less than nine carbon atoms; X is a halide; each Y is independently selected from a group consisting of hydrogen and lower alkyl radicals; n=1, 2, or 3; a=0, 1 or 2; b=1, 2, or 3; and a+b=1, 2, or 3.

In carrying out the reaction of the present invention, the unsaturated olefinic nitrile, the silicon hydride and the catalyst mixture are contacted in a suitable reaction vessel. The type of reaction vessel is not critical as long as free oxygen can essentially be eliminated from contact with the reactants and catalyst mixture. The process can be run as a batch process or as a continuous process. A preferred process is where the reaction is conducted under homogeneous conditions in a continuous flow pressure coil.

The benefits of the instant invention are achieved by running the process in an essentially oxygen free environment. By "essentially oxygen free environment" is meant, the free oxygen content of the environment in which the process is run is reduced below that of normal air. By "free oxygen," it is meant oxygen that is not present in combination with other elements. It is preferred that the "essentially oxygen free environment" contain less than about 0.5 percent free oxygen. The reaction vessel can be reduced in free oxygen by standard means, for example, purging with an inert gas such as nitrogen, argon, or helium or by vacuum evacuation. Preferred is when the reactor is purged with nitrogen, prior to addition of reactants and catalyst, and maintained under a flow of nitrogen adequate to provide an essentially oxygen free environment during conduct of the described process. The reduction of free oxygen in the process can increase the reaction rate and improve process yield.

The time required for effecting the reaction varies depending on the particular reactants, the particular catalyst mixture employed, and the temperature of the reaction. In general, reaction times of 0.2 to 18 hours are useful. A preferred reaction time is about 0.5 to 3.0 hours.

The temperature for conducting the process may be within a range of about 0° C. to about 200° C. It is preferred that the temperature be within a range of about 40° C. to 150° C. Generally, higher temperatures allow the use of a catalyst with a lower copper concentration, but at temperatures above about 150° C. undesired by-products may be produced.

The silicon hydride, Formula 2, employed in the present invention can contain from one to three silicon-bonded hydrogens and from one to three silicon-bonded halide atoms. The halide atom, X, can be selected from the group consisting of fluoride, chloride, bromide and iodide. The preferred halide is chloride.

The silicon hydride can contain up to two radicals, R, selected from a group comprising monovalent hydrocarbon radicals, alkoxy radicals, aryloxy, and substituted monovalent hydrocarbon radicals, where R is inert with respect to the addition reaction. The radical, R, can be, for example, alkyl radicals, e.g., methyl, ethyl, butyl, octyl, and octadecyl. The preferred alkyl is when R is a lower alkyl radical containing from 1 to 8 carbon atoms. The radical, R, can be, for example, aryl radicals, e.g. phenyl, naphthyl, diphenyl, tolyl, xylyl, and ethylphenyl. The preferred aryl radical is phenyl. The radical, R, can be, for example, aralkyl, e.g., benzyl and phenylethyl; haloaryl, e.g., chlorophenyl, dibromophenyl and chloronaphthyl; cyanoalkyl, e.g., $\beta$-cyanoethyl, $\beta$-cyanopropyl, and $\beta$-cyanobutyl; cycloalkyl, e.g., cyclohexyl and cycloheptyl; alkenyl, e.g., vinyl and allyl; substituted alkyl, e.g. 3,3,3-trifluoropropyl; alkoxy, e.g. methoxy, ethoxy, and propoxy; and aryloxy, e.g. phenoxy. Most preferred is when the radical, R, is methyl. The preferred silicon hydride is selected from a group consisting of methyldichlorosilane and trichlorosilane.

The silicon hydride is contacted with an $\alpha,\beta$-unsaturated olefinic nitrile, described by Formula 3 and containing substituent Y, where each Y is independently selected from a group consisting of hydrogen and lower alkyl radicals. By "lower alkyl radicals" is meant, alkyl radicals having from 1 to 8 carbon atoms. The unsaturated olefinic nitrile can be, for example, acrylonitrile, methacrylonitrile, crotononitrile, ethylacrylonitrile, 1-cyanobutene-1, or 2-cyanooctene-1.

The silicon hydride and unsaturated olefinic nitrile are contacted in the presence of a catalyst comprising a mixture of a diamine with copper metal or a copper compound. The diamine is as described by Formula 4, where $R^1$ is a lower alkyl radical of 1 to 8 carbon atoms; $R^2$ is selected from a group consisting of hydrogen, lower alkyl radicals of 1 to 8 carbon atoms, aminoalkyl radicals, alkylaminoalkyl radicals, dialkylaminoalkyl radicals, and mixtures thereof; and $R^3$ is an unsubstituted bivalent radical selected from the group consisting of alkylenes and alkenylenes of less than 9 carbon atoms.

The diamine can be, for example, N,N,N',N'-tetramethylethylenediamine, N,N,N',N'-tetraethylethylenediamine, N,N,N'-trimethylethylenediamine, N,N-dimethyl-yl-N',N'-diethylethylenediamine, N,N-dimethylethylenediamine, N-methyl-N,N',N'-triethylethylenediamine, N,N,N',N",N"-pentamethyldiethylenetriamine, N,N,N'-trimethyl-N'-ethylethylenediamine, N,N,N',N'-tetramethylmethylenediamine, N,N',N",N"-tetramethyldiethylenetriamine, N,N,N',N'-tetramethyldiethylenetriamine, and N-methylhexamethylenediamine. The preferred diamine is N,N,N',N'-tetramethylethylenediamine.

The catalyst comprises a mixture of the diamine with copper metal or a copper compound. The mixture can be preformed and added to the reaction vessel or the diamine and copper metal or copper compound can be added separately to the process.

The copper metal may be added to the reactor as a particulate, for example, a powder. Although the particle size of the elemental copper is not critical, preferred is when the elemental copper has an average particle size less than about 325 mesh. Preferred is when the elemental copper has a particle size less than about 100 mesh. The copper compounds may be soluble or insoluble in the reaction mixture, depending upon the silicon hydride, unsaturated olefinic nitrile, and diamine present.

Although not necessary, it is preferred that the contents of the reactor be mixed when the instant process is run as a batch process. Mixing of the reactor contents is especially important when the catalyst is in a particulate or insoluble form. Mixing can be accomplished by standard means, for example, mechanical stirring, refluxing, sonification, or turbulent flow.

The copper compounds can be inorganic and organic compounds of copper(I) and copper(II). When the copper compound is an organic compound, it is preferred that each organic constituent be of less than about 25 carbon atoms.

The inorganic compound of copper can be selected from a group consisting of, for example, copper halide, copper oxide; copper sulfate, copper sulfide, and copper cyanide compounds; Cu(I) thiocyanide; and copper chromium compounds. The copper halide can be, for example, Cu(I) chloride, Cu(I) bromide, Cu(I) iodide, Cu(I) fluoride, Cu(II) chloride, Cu(II) bromide, Cu(II) iodide, and Cu(II) fluoride. The copper oxide can be, for example, Cu(I) oxide and Cu(II) oxide. The copper sulfate can be, for example, Cu(I) sulfate and Cu(II) sulfate. The copper sulfide can be, for example, Cu(I) sulfide and Cu(II) sulfide. The copper cyanide compound can be, for example, Cu(I) cyanide and Cu(II) cyanide. The copper chromium compounds can be, for example: Cu(II) chromate, e.g., $CuCrO_4 \cdot 2CuO \cdot 2H_2O$; Cu(II) dichromate, e.g., $CuCr_2O_7 \cdot 2H_2O$; and Cu(I) chromite, e.g., $Cu_2Cr_2O_4(2CuOCr_2O_3)$.

The preferred inorganic copper compound is selected from a group consisting of Cu(I) oxide, Cu(II) oxide, Cu(I) chloride, and Cu(II) chloride. The most preferred copper compound is Cu(I) oxide.

The copper compound can be an organic copper compound. Preferred is when the organic copper compound is a di-coordinate organic copper compound. By "di-coordinate organic copper compound" is meant compounds of general formula $Cu(R^4)_2$; where $R^4$ is a radical of formula:

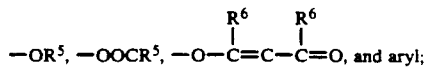

where $R^5$ is selected from a group consisting of alkyl, alkenyl, and aryl radicals of less than 25 carbon atoms and $R^6$ is selected from a group consisting of hydrogen and hydrocarbon radicals of less than seven carbon atoms.

The di-coordinate organic copper compound can be, for example. Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) naphthanate, and Cu(II) phenylate.

The copper or copper compound can be retained on a solid support. The method of retention of the copper or copper compound on the solid support is not critical to the present invention. It is preferred that copper or the copper compound not be released from the solid support during conduct of the process. The copper or copper compound may be retained on or within the solid support by standard means, for example, adsorption, ionic bonding, covalent bonding, or physical entrapment. The solid support material can be any material capable of retaining the copper or copper compound under process conditions. The solid support material can be, for example, silicon metalloid, silica, silica gel, alumina, carbon, graphite, ceramic, or zeolite. The silica can be, for example, a fumed or precipitated silica. Preferred is when the solid support material is metallurgical grade silicon or silica gel.

The solid support material can be in the form of, for example, flakes, chips, particles, powders, pellets, and tablets. Preferred is when the solid support material is less than about one centimeter in diameter. More preferred is when the solid support material is less than about 0.5 centimeter in diameter. The lower size limit for the solid support material is determined by the practicalities of retaining, recovering, and handling of the material.

Copper supported on metallurgical grade silicon or on silica gel is a preferred supported copper component for the catalyst. Copper halides and copper oxides supported on silica are preferred supported copper compounds.

A useful concentration of copper retained on the solid support, either in the form of elemental copper or copper compound, is where the weight of copper is within a range of about 0.5 to 30 weight percent of the weight of the solid support. Lower concentrations of copper may be used, but the product production rate may be reduced. Preferred is when the concentration of copper retained on the solid support, either in the form of elemental copper or copper compound, is within a range of 1 to 5 weight percent of the weight of the solid support.

The catalyst can comprise on a molar basis about 0.1 to 20 moles of diamine per mole of copper, the copper present either as copper or copper compound. In general, as the temperature of the process is increased a lower mole ratio of diamine to copper is required. A preferred mole ratio of diamine to copper is within a range of about 0.2 to 2.0.

The amount of catalyst employed in relation to the amount of silicon hydride and unsaturated olefinic nitrile may be varied within extremely wide limits. However, it is preferred to run the process under conditions where the mole ratio of copper to unsaturated olefinic nitrile is in a range of about 0.01 to 1.0. A more preferred ratio of copper to unsaturated olefinic nitrile is in a range of about 0.08 to 0.5.

The present process may be run as a continuous process where the copper or copper compound is in a particulate form or on a solid support. In this situation, the copper or copper compound can be separately contacted with a diamine at molar ratios as described for a batch process. It is believed that the diamine complexes with the copper and is partially retained by the insoluble or supported copper or copper compound to maintain an active catalyst mixture. However, during the continuous process it may be necessary to reactivate the catalyst by addition of diamine to the process. The diamine required to reactivate the catalyst may be added separately to the insoluble or supported copper or copper compound or may be added as a mixture with feed materials to the process.

The ratio of the silicon hydride to the unsaturated olefinic nitrile may be varied within wide limits. However, since the preferred process involves adding one mole of the silicon hydride to one mole of the unsaturated olefinic nitrile, in the preferred embodiment of the invention about equimolar amounts of these reactants are employed. The use of molar excesses of either of the two reactants is not precluded, however no particular advantage is derived from employing a molar excess of either reactant.

The described method is applicable to the production of β-cyanoalkylsilanes, as described by Formula 1. The preferred β-cyanoalkylsilanes, within the scope of Formula 1, are β-cyanoethylmethyldichlorosilane and β-cyanotrichlorosilane. However, the instant process is also applicable to the preparation of hydrolyzable silanes containing more than one silicon-bonded β-cyanoalkyl radical, for example, bis-(β-cyanoethyl)dichlorosilane and tris-(β-cyanoethyl)chlorosilane, by the addition of one mole of silicon bi- or tri-hydride to more than one mole of unsaturated olefinic nitrile. Other examples of β-cyanoalkylsilanes that can be made by the method of this invention, within the scope of Formula 1, are: β-cyanoethyltrichlorosilane, β-cyanoethylmethyldichlorosilane, β-cyanoethylethyldichlorosilane, β-cyanopropyltrichlorosilane, β-cyanobutyloctyldichlorosilane, β-cyanoethylphenyldichlorosilane, β-cyanoethyldiphenylchlorosilane, β-cyanoethylmethylphenylchlorosilane, β-cyanoethylcyclohexyliodochlorosilane, α-ethyl-β-cyanoethylmethyldichlorosilane, and β-cyanoethylvinyldichchlorosilane, and β-cyanoethylchlorosilane.

In order that those skilled in the art may better understand how the present invention may be practiced, the following examples are given. These examples are given for illustration and are not meant to be limiting on the instant claims.

EXAMPLE 1

The effects of a nitrogen purge and blanket at the reaction vessel condenser on product yield was evaluated. The reactor consisted of a 500 ml vessel equipped with a mechanical stirrer, addition funnel, and a condenser separately connected to a nitrogen purge line. All reagents were weighed in air. The process was run by adding 1.1 moles of methyldichlorosilane, 1.0 moles of acrylonitrile, 0.237 moles of tetramethylethyldiamine, and 0.086 moles of cuprous oxide to the reaction vessel. A nitrogen blanket was established at the condenser and the process run under the time and temperature conditions described in Table 1. The reaction temperature (Rx Temp.) varied between the described limits, with generally the process being started at room temperature and a subsequent exotherm allowed to occur followed by additional heating by means of a heating mantle around the reactor. The contact time of the reactants is presented under the heading "Rx Time."

The material collected in a collection flask connected to the condenser was analyzed by gas chromatography employing a flame ionization detector (GC-FID). The percent conversion of the acrylonitrile added to the reactor to β-cyanoethylmethyldichlorosilane is presented in the column labelled "% CEMDS."

TABLE 1

Effect of Nitrogen Blanket at The Condenser on Process Yield

| Run No. | Rx Temp. (°C.) | Rx Time (h) | % CEMDS |
|---|---|---|---|
| 128 | 23–85 | 2.75 | 56.0 |
| 142 | 18–83 | 4.5 | 47.8 |

EXAMPLE 2

For this run, the reactants and procedures were the same as for Example 1 except that the reactor was purged with nitrogen prior to start of the reaction and a nitrogen blanket was established at the condenser during the run. The results of this run are presented in Table 2. The headings for Table 2 are as previously described for Table 1.

TABLE 2

Effects of Nitrogen Purge of Reactor on Product Yield

| Run No. | Rx Temp. (°C.) | Rx Time (h) | % CEMDS |
|---|---|---|---|
| 147 | 43–100 | 5.5 | 77.0 |

EXAMPLE 3

For these runs, the reactants and procedures were the same as for Example 2 except that all reagents were distilled under nitrogen and transferred to the reactor under nitrogen. The results of these runs are presented in Table 3. The headings for Table 3 are as previously described for Table 1.

TABLE 3

Effects of Distilling Reagents Under Nitrogen

| Run No. | Rx Temp. (°C.) | Rx Time (h) | % CEMDS |
|---|---|---|---|
| 13 | 47–112 | 5.5 | 81.0 |
| 15 | 46–106 | 3.6 | 78.0 |

What is claimed is:

1. A process for preparation of β-cyanoalkylsilanes of formula

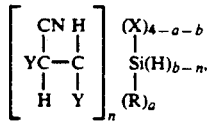

the process comprising:

contacting, in an essentially oxygen free environment, a silicon hydride of formula

with an unsaturated olefinic nitrile of formula

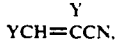

in the presence of a catalyst comprising a diamine of formula

and a copper source selected from a group consisting of copper and copper compounds; at a temperature within a range of about 0° C. to 200° C.;

where each R is independently selected from a group consisting of monovalent hydrocarbon radicals, substituted monovalent hydrocarbon radicals, alkoxy radicals, and aryloxy radicals; $R^1$ is a lower alkyl radical; $R^2$ is selected from a group consisting of hydrogen, lower alkyl radicals, aminoalkyl radicals, alkylaminoalkyl radicals, dialkylaminoalkyl radicals, and mixtures thereof; $R^3$ is an unsubstituted bivalent radical selected from a group consisting of alkylenes and alkenylenes of less than 9 carbon atoms; X is a halide; each Y is independently selected from a group consisting of hydrogen and lower alkyl radicals of 1 to 8 carbon atoms; n=1, 2, or 3; a=0, 1, or 2; b=1, 2, or 3; and a+b=1, 2, or 3.

2. A process according to claim 1, where the essentially oxygen free environment contains less than about 0.5 percent free oxygen.

3. A process according to claim 1, where the temperature is within a range of about 40° C. to 150° C.

4. A process according to claim 1, where the halide is chloride.

5. A process according to claim 4, where R is methyl.

6. A process according to claim 1, where the silicon hydride is selected from a group consisting of methyldichlorosilane and trichlorosilane.

7. A process according to claim 1, where the unsaturated olefinic nitrile is selected from a group consisting of acrylonitrile, methacrylonitrile, crotononitrile, ethylacrylonitrile, 1-cyanobutene-1, and 2-cyanooctene-1.

8. A process according to claim 1, where the unsaturated olefinic nitrile is acrylonitrile.

9. A process according to claim 1, where the diamine is N,N,N',N'-tetramethylethylenediamine.

10. A process according to claim 1, where the copper source is copper metal.

11. A process according to claim 1, where the copper source is selected from a group consisting of inorganic copper (I) and inorganic copper (II) compounds.

12. A process according to claim 11, where the copper source is selected from a group consisting of Cu(I) oxide, Cu(II) oxide, Cu(I) chloride, and Cu(II) chloride.

13. A process according to claim 12, where the copper source is Cu(I) oxide.

14. A process according to claim 1, where the copper source is a di-coordinate organic copper compound selected from a group consisting of Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) naphthanate, and Cu(II) phenylate.

15. A process according to claim 1, where the catalyst comprises about 0.2 to 2.0 moles of the diamine per mole of copper.

16. A process according to claim 1, where the mole ratio of copper to unsaturated olefinic nitrile is within a range of about 0.08 to 0.5.

17. A process according to claim 1, where the β-cyanoalkylsilane is β-cyanoethylmethyldichlorosilane.

18. A process according to claim 1, where the β-cyanoalkylsilane is β-cyanoethyltrichlorosilane.

19. A process according to claim 1, where the silicon hydride is methyldichlorosilane, the olefinic nitrile is acrylonitrile, the diamine is N,N,N',N'-tetramethylethyllenediamine, the copper source is Cu(I) oxide, and the temperature is within a range of about 40° C. to 150° C.

20. A process according to claim 1, where the process is run in a continuous flow pressure coil.

21. A process according to claim 1, where the copper source is retained on a solid support.

22. A process according to claim 21, where the solid support is selected from a group consisting of silicon and silica gel.

23. A process according to claim 21, where the copper source is copper metal.

24. A process according to claim 21, where the copper source is a copper compound selected from a group consisting of Cu(I) oxide, Cu(II) oxide, Cu(I) chloride, and Cu(II) chloride.

25. A process according to claim 21, where the copper source is Cu(II) oxide and the solid support is silica gel.

26. A process according to claim 21, where the copper source is copper and the solid support is silicon.

* * * * *